(12) United States Patent
Zhao et al.

(10) Patent No.: US 7,709,794 B2
(45) Date of Patent: May 4, 2010

(54) DEFECT DETECTION USING TIME DELAY LOCK-IN THERMOGRAPHY (LIT) AND DARK FIELD LIT

(75) Inventors: Guoheng Zhao, Milpitas, CA (US);
Geordie Zapalac, Santa Cruz, CA (US);
Samuel Ngai, San Francisco, CA (US);
Mehdi Vaez-Iravani, Los Gatos, CA (US); Ady Levy, Sunnyvale, CA (US);
Vineet Dharmadhikari, San Jose, CA (US)

(73) Assignee: KLA-Tencor Corporation, San Jose, CA (US)

(*) Notice: Subject to any disclaimer, the term of this patent is extended or adjusted under 35 U.S.C. 154(b) by 106 days.

(21) Appl. No.: 12/026,539

(22) Filed: Feb. 5, 2008

(65) Prior Publication Data

US 2010/0073665 A1 Mar. 25, 2010

(51) Int. Cl.
*G01J 5/00* (2006.01)
(52) U.S. Cl. .................................. 250/338.1; 250/334
(58) Field of Classification Search ................. 250/340, 250/341, 338.1, 334
See application file for complete search history.

(56) References Cited

U.S. PATENT DOCUMENTS

| 5,798,829 | A | * | 8/1998 | Vaez-Iravani | 356/237.1 |
|---|---|---|---|---|---|
| 6,000,844 | A | * | 12/1999 | Cramer et al. | 374/5 |
| 6,958,771 | B2 | * | 10/2005 | Takeuchi et al. | 348/194 |
| 7,463,362 | B2 | * | 12/2008 | Lasker et al. | 356/497 |
| 2004/0050164 | A1 | * | 3/2004 | Bates | 73/587 |

OTHER PUBLICATIONS

Kaes et al., "Light Modulated Lock-in Thermography for Photosensitive pn-Structures and Solar Cells", Progress in Photovoltaics: Research and Applications; 2004: vol. 12, pp. 355-363.*

* cited by examiner

*Primary Examiner*—David P Porta
*Assistant Examiner*—Yara B Green
(74) *Attorney, Agent, or Firm*—Bever, Hoffman & Harms, LLP; Jeanette S. Harms

(57) ABSTRACT

To increase inspection throughput, the field of view (FOV) of an IR camera can be moved over the sample at a constant velocity. Throughout this moving, a modulation (e.g. optical or electrical) can be provided to the sample and IR images can be captured using the IR camera. Moving the FOV, providing the modulation, and capturing the IR images can be synchronized. The IR images can be filtered to generate the time delay LIT, thereby providing defect identification. In one embodiment, this filtering accounts for the number of pixels of the IR camera in a scanning direction. For the case of optical modulation, a dark field region can be provided for the FOV throughout the moving, thereby providing an improved signal-to-noise ratio (SNR) during filtering.

19 Claims, 10 Drawing Sheets

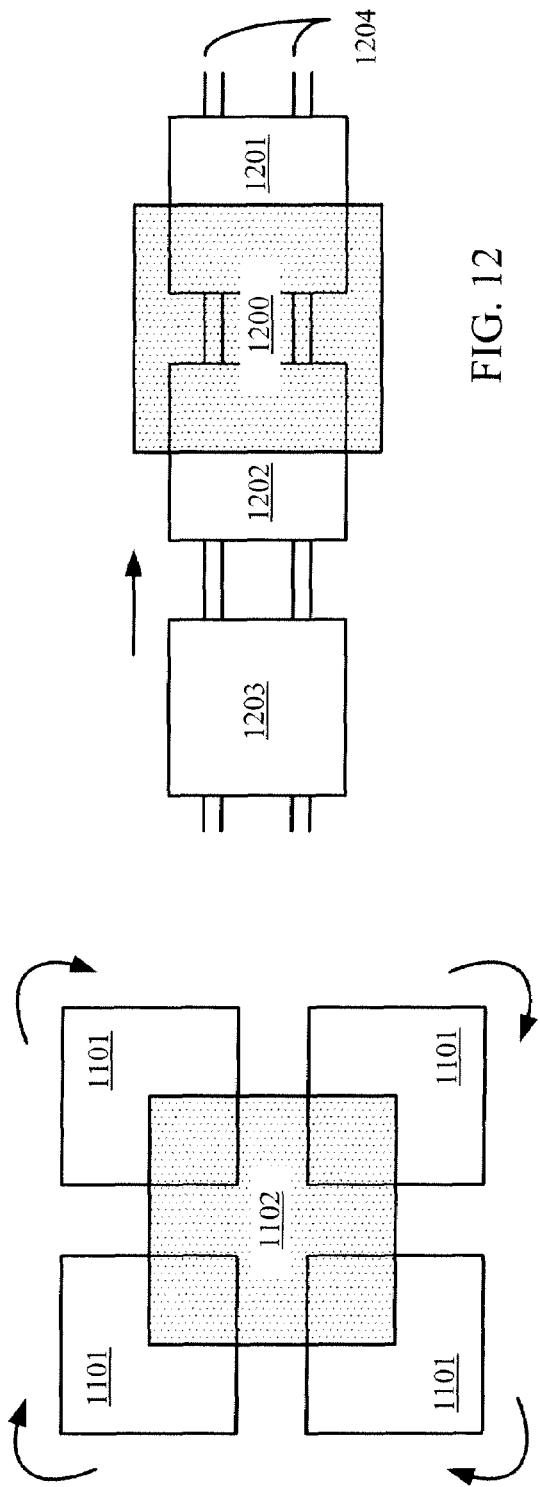
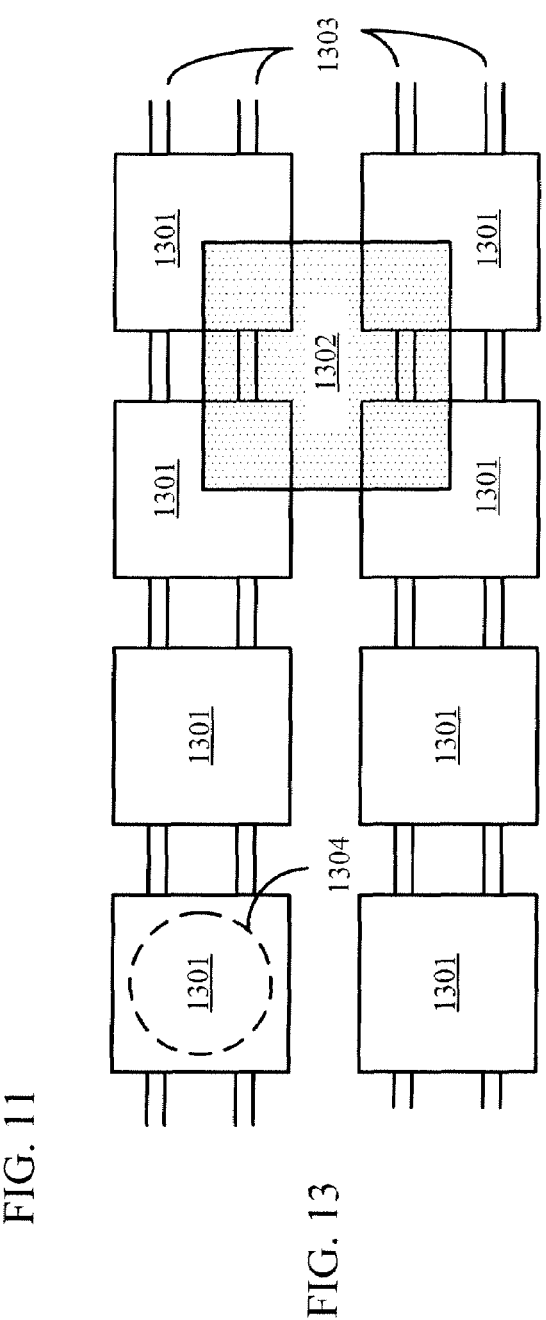
FIG. 12
FIG. 11
FIG. 13

DEFECT DETECTION USING TIME DELAY LOCK-IN THERMOGRAPHY (LIT) AND DARK FIELD LIT

BACKGROUND OF THE INVENTION

1. Field of the Invention

The present invention relates to defect detection on a sample using time delay lock-in thermography (LIT) to ensure high throughput and improve defect detection sensitivity in production environments. Dark field illumination can be used to minimize background noise in certain LIT embodiments.

2. Related Art

During the manufacturing process samples may develop localized electrical defects that cause current leakage. Exemplary samples could include photovoltaic materials (e.g. 156 mm×156 mm wafers or 2160 mm×2460 mm panels), semiconductor wafers, or printed circuit boards (PCBs). Electrical defects, such as shunts and localized weak diodes, leak current and therefore can reduce the efficiency of the sample or even jeopardize the functioning of the devices on the sample. Therefore, it is highly desirable to accurately detect the positions of such electrical defects.

Defects have high current density passing through them and therefore heat up to a higher temperature than that of the sample. These temperature changes can be detected in the image from a focal plane array (FPA) IR camera. However, the change in temperature at a defect may be 5 orders of magnitude smaller than the background in the image. Thus, separating the defects from background noise may be challenging.

Lock-in thermography (LIT) is one known method for locating such defects. In LIT, the sample is modulated, e.g. by direct current injection into the sample or by photocurrent generated from illumination of the sample. When the modulation is by illumination, the method is sometimes called illuminated lock-in thermography (ILIT). Temperature changes caused by heating of the sample from the injected current or photocurrent are modulated at the same frequency. With either form of modulation, multiple frames of IR images are captured while the sample remains stationary.

Due to the shot noise of background IR radiation from the sample at room temperature as well as the very small temperature difference between the defects and the rest of the sample, and the limited dynamic range of the IR imaging sensor, a large number of images of the same field of view (FOV) are needed to average out the background noise, thereby improving the signal to noise ratio (SNR). Although the captured images are taken from the identical spatial location, they are a function of time as the temperature of the sample oscillates at the frequency of modulation. In a typical embodiment, the images are filtered by multiplying each image by a weighting factor that varies sinusoidally in time at the same frequency as the modulation or "lock-in" frequency. In general, the improvement of SNR is proportional to the square root of N, wherein N is the total number of frames.

Conventional LIT requires that the sample remains stationary while the IR camera acquires the necessary number of images for lock-in averaging. If the size of the sample is greater than the field of view (FOV) of the camera, the sample (or the IR camera) needs to move to a completely different location to capture a new set of IR images after one set of images is captured for one location on the sample. Unfortunately, this stop-go time as well as the settling time (which includes repositioning with its attendant velocity ramp up and ramp down) takes a large portion of the total inspection time, especially for very large samples that can be greater than 2 m×2 m in size, thereby undesirably reducing throughput. This overhead in conventional lock-in thermography becomes a significant limiting factor of inspection throughput.

Therefore, a need arises for a technique of detecting defects on a sample that increases inspection throughput compared to conventional LIT while maintaining its accuracy.

SUMMARY OF THE INVENTION

Conventional lock-in thermography (LIT) techniques require that the sample remains stationary while the IR camera acquires the necessary number of images for lock-in integration. After one set of images is acquired, the sample is replaced or repositioned to capture IR images for a different sample or location. This stationary and repositioning time significantly reduces inspection throughput.

To increase inspection throughput, a method of performing time delay LIT on a sample is provided. In this method, the FOV of an IR camera can be moved over the sample at a constant velocity. Throughout this moving, a modulation (e.g. optical or electrical) can be provided to the sample and IR images can be captured using the IR camera. Moving the FOV, providing the modulation, and capturing the IR images can be synchronized. The IR images can be filtered to generate the time delay LIT image, thereby providing defect identification. In one embodiment, this filtering can include sinusoidal weighting at the lock-in frequency that takes into account the number of pixels of the IR camera in a scanning direction.

Advantageously, this time delay LIT can be used on various types of samples, e.g. semiconductor wafers, photovoltaic wafers, large panels of photovoltaic material, continuous webs of photovoltaic material, and printed circuit boards. Further, the moving can be done using any efficient moving components, e.g. a scanning stage, bi-directional linear stages in a gantry system, a gantry bridge, a conveyor, and/or at least one roller.

In one embodiment, the FOV can be located within a dark field region throughout the moving, thereby providing an improved signal-to-noise ratio (SNR) during filtering. This dark field technique can also be used in what would otherwise be standard ILIT. In this method, the sample is illuminated outside the camera FOV. IR images can be captured using the IR camera, wherein providing the modulation and capturing the IR images are synchronized. The IR images can be filtered to generate the time-averaged image, thereby providing defect identification. Advantageously, the sample can be rotated or moved linearly to reposition the FOV and the dark field region on another section of the sample. At this point, the steps of providing the modulation, capturing the IR images, and filtering the IR images can be repeated.

This dark field technique can be used with various types of samples, e.g. semiconductor wafers, photovoltaic wafers, photovoltaic panels, continuous webs of deposited photovoltaic material, and printed circuit boards. Positioning and rotating can include using a scanning stage, bi-directional linear stages in a gantry system, a gantry bridge, a conveyor, a rotating chuck, and/or at least one roller.

A system for performing the time delay LIT can include an IR camera for capturing images of the sample. Scanning components can move the FOV of the IR camera over the sample at a constant velocity. Modulation components can provide a modulation to the sample when moving the FOV. A clock source can synchronize the capturing of images, the moving of the FOV, and the source of the modulation. An image processor can receive the captured images and generate the time delay LIT image to provide defect detection. In one embodiment, a light shield is used to shadow the FOV from the source of illumination for ILIT.

A system for performing dark field ILIT can include positioning components for positioning the FOV of the IR camera over the sample. Optical modulation components can provide an optical modulation to the sample after positioning the FOV. A light directing component can provide a dark field region for the FOV. A clock source can synchronize the image acquisition to the modulation. An image processor can receive the captured images and generate the time delay ILIT image to detect defects on the sample. The light directing component can include a light shield or a light pipe.

BRIEF DESCRIPTION OF THE FIGURES

FIGS. 11 and 12 illustrate other exemplary dark field ILIT configurations using rotational and linear movements, respectively.

FIG. 13 illustrates the dark field ILIT configuration of FIG. 11 in a system that includes both rotational and linear movements.

DETAILED DESCRIPTION OF THE FIGURES

Conventional lock-in thermography (LIT) systems require that the sample remains stationary while the IR camera acquires the necessary number of images for lock-in integration. After one set of images are captured for one location on the sample, the sample is repositioned to capture IR images for a completely different location. This stationary and repositioning time significantly reduces inspection throughput.

Figure 1:
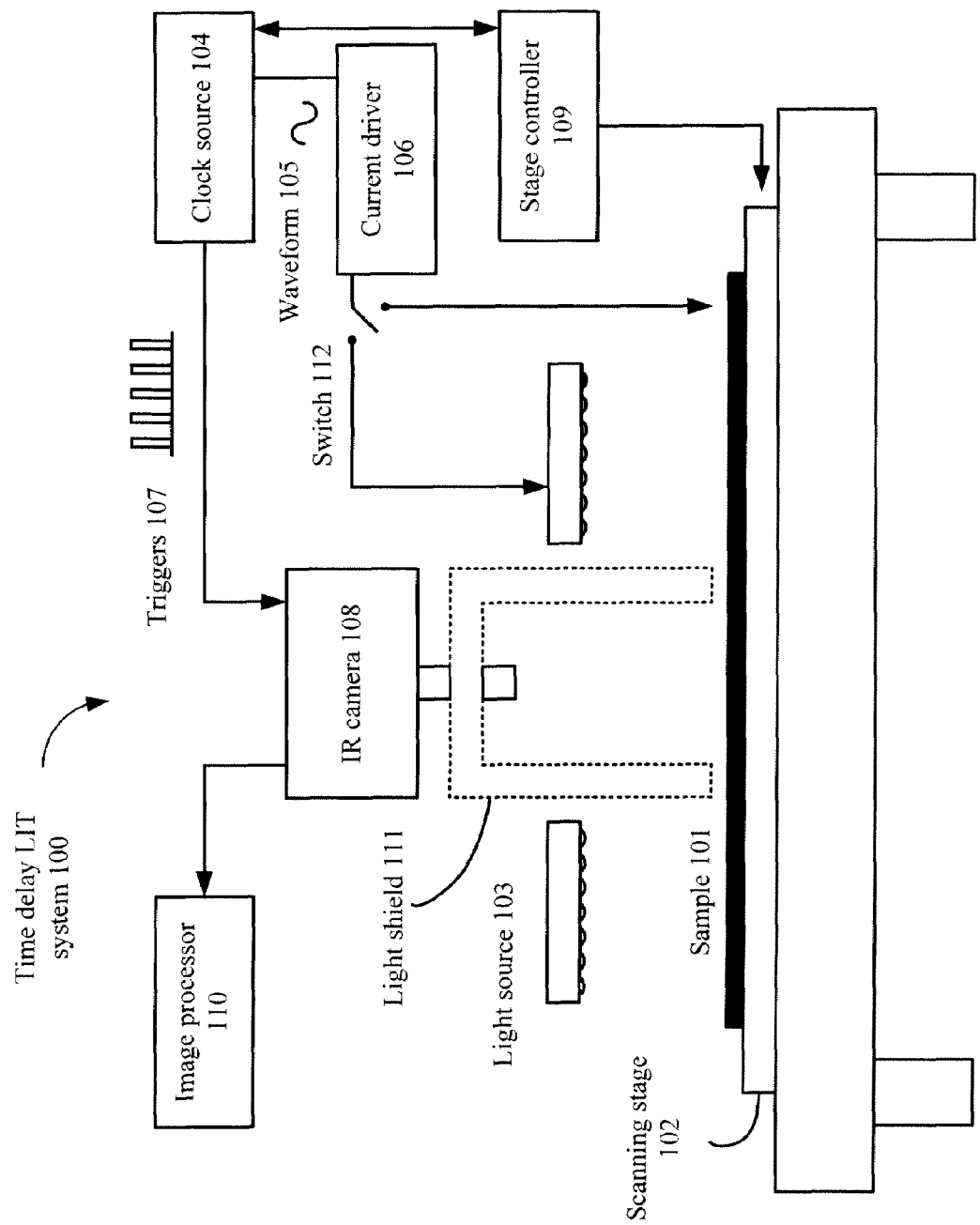
FIG. 1 illustrates an exemplary time delay ILIT system including a dark field illumination.

FIG. 1 illustrates an exemplary time delay LIT system 100 that can significantly increase inspection throughput. In this embodiment, a sample 101 is positioned on an x-y scanning stage 102. Applying a modulation to the sample can be performed optically (e.g. by using a modulated illuminating light source) or electrically (e.g. by directly applying a current modulation to the sample). In one embodiment, a current driver 106 can be selectively connected to a light source 103 or directly connected to sample 101 using a switch 112. In other embodiments, system 100 can include the components to provide only one type of modulation, i.e. current driver 106 and light source 103 or only current driver 106, and eliminate switch 112.

Light source 103 can be constructed using multiple LED modules. However, in other embodiments, light source 103 can be implemented using a standard white light source modulated by a chopper, lasers that are directly modulated, or Q-switch lasers.

A clock source 104 can generate a waveform 105, which is provided to current driver 106. This waveform is converted to a current that, as described above, can drive light source 103 or is directly connected to sample 101. Clock source 104 can also generate triggers 107 that activate an IR camera 108 to capture IR images, which in turn are provided to an image processor 110. Clock source 104 can be connected to a stage controller 109, which outputs a positioning encoder pulse to scanning stage 102. In this configuration, as described in further detail below, clock source 104 can advantageously ensure that the speed of sample motion is properly synchronized to the image acquisition frame rate and the modulation rate. In other embodiments, the encoder signal of the stage controller can be used as the clock signal to trigger a function generator for providing modulation to the sample, and also for triggering the IR camera for image acquisition.

Figure 2A:
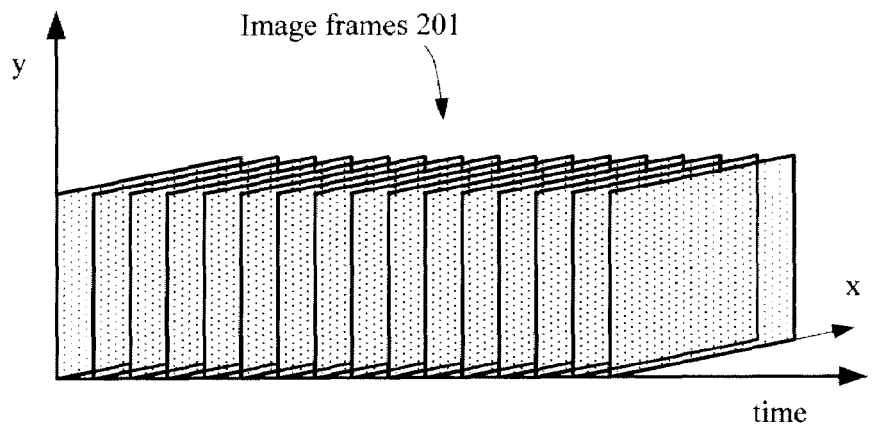
FIG. 2A illustrates an exemplary acquisition of frames of IR images using conventional LIT.

FIG. 2A illustrates an exemplary acquisition of frames 201 of IR images using conventional LIT. As described above, to acquire frames 201, the sample is modulated with a periodic signal, e.g. a sinusoidal function, while the sample remains stationary. Frames 201 are then processed by applying a Fourier filter in time domain at the frequency of modulation.

In one embodiment, the discrete sine and cosine transforms are defined as follows.

$$S_{m,n} = \frac{1}{N_F} \sum_{i=1}^{N_F} I_{m,n}^i \sin\left(2\pi \frac{f_1}{f_2}(i-1)\right)$$ Equation 1

$$C_{m,n} = \frac{1}{N_F} \sum_{i=1}^{N_F} I_{m,n}^i \cos\left(2\pi \frac{f_1}{f_2}(i-1)\right)$$ Equation 2

Where $I_{m,n}^i$ is the pixel value of the (m,n)th pixel of the ith frame, m=1, 2, ... $N_x$, n=1, 2, ... $N_y$, i=1, 2, 3 ..., $f_1$ is the frequency of modulation, $f_2$ is the frame rate (preferably an even integer multiple of $f_1$), P is the pixel size on the sample, $N_x$ and $N_y$ are the number of pixels in one frame in the x and y directions, and $N_F$ is the total number of frames (e.g. an integer multiple of the number of modulation cycles).

Note that certain samples may respond differently to different phases of modulation. However, notably, the sine and cosine transforms can be combined to generate an amplitude independent of phase. Specifically, using the values for $S_{m,n}$ and $C_{m,n}$ as computed by Equations 1 and 2, the amplitude A and phase image φ are given by:

$$A = \sqrt{S^2 + C^2}$$ Equation 3

$$\phi = \tan^{-1}\frac{S}{C}$$ Equation 4

Figure 2B:
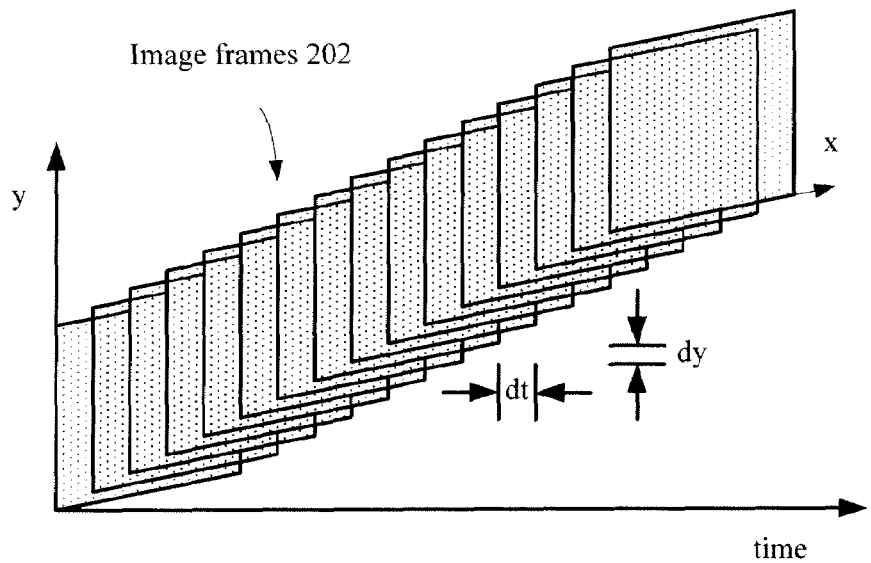
FIG. 2B illustrates an exemplary acquisition of frames of IR images using time delay LIT.

In contrast, FIG. 2B illustrates an exemplary acquisition of frames 202 of IR images using time delay LIT. As described above in reference to FIG. 1, unlike conventional LIT, multiple image frames are acquired in time delay LIT while the sample moves at a constant speed (thus, the imaged locations as measured in a y direction change over time). Advantageously, the speed of motion (dy/dt) can be synchronized to the frame rate of the image acquisition.

In one embodiment, the sample can move by a distance of one pixel within the time duration of one frame. Thus, in one embodiment, the total number of frames for time delay LIT is the same as the number of pixels of the FOV of the IR camera in the scan direction. Note that image capture can begin with the FOV only slightly overlapping the sample (e.g. by one pixel or less) to ensure that even the edges of the sample are in fact imaged multiple times.

In other embodiments, the distance that a sample moves between two consecutive frames can be integer multiples, e.g. 1, 2, 3 . . . pixels, which allows higher inspection speed at a fixed frame rate. The integer multiple approach provides lower sensitivity because the total number of frames for LIT is reduced by a factor equal to the number of pixels moved. In yet another embodiment, the distance that the sample moves between two consecutive frames can be less than 1 pixel (e.g. generically 1/N pixel: ⅕ pixel, ¼ pixel, ⅓ pixel, ½ pixel, etc.), which allows higher inspection accuracy, but results in slower inspection speed. In one embodiment, a predetermined number of frames can be designated for capture during each modulation cycle (e.g. at least 4), thereby determining inspection accuracy as well as the allowed inspection speed.

Figure 2C:
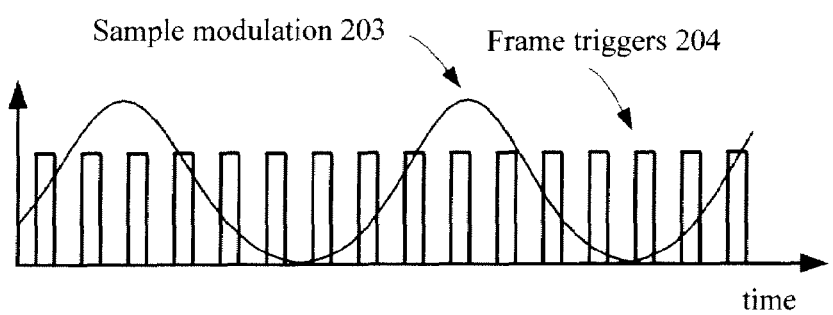
FIG. 2C illustrates an exemplary sample modulation relative to a plurality of frame triggers.

In accordance with any embodiment of time delay LIT, as the sample is modulated at a fixed frequency, each imaging pixel of the sample is imaged multiple times as the sample continuously moves across the field of view (FOV) of the IR camera. Therefore, an image for each imaging pixel is read out multiple times by a line of the pixels of the IR imaging sensor, which can form part of the IR camera. The captured images in a time delay LIT image are given by the following sine and cosine transforms, which together provide Fourier filtering.

$$S_{m,i} = \frac{1}{N_Y}\sum_{n=1}^{N_Y} I_{m,n}^{(i+n-1)}\sin\left[2\pi(i-1+n-1)\frac{f_1}{f_2}\right]$$ Equation 5

$$C_{m,i} = \frac{1}{N_Y}\sum_{n=1}^{N_Y} I_{m,n}^{(i+n-1)}\cos\left[2\pi(i-1+n-1)\frac{f_1}{f_2}\right]$$ Equation 6

Where $I_{m,n}^{(i+n-1)}$ is the pixel value of the (m,n)th pixel of the (i+n−1)th frame of the IR images, i=1, 2 . . . , m=1, 2, . . . $N_x$, n=1, 2, . . . $N_y$, $f_1$ is the frequency of modulation, and $f_2$ is the frame rate. Preferably $f_2$ is an even integer (≧4) multiple of $f_1$. $N_x$ and $N_y$ are the number of pixels in one frame in the x and y directions. Note that the index n appears in both the subscripts of pixel index and the superscript of frame index of $I_{m,n}^{(i+n-1)}$, which defines the tracking each pixel of a specific spatial position as it moves across the FOV of the IR camera. The speed V of the moving sample is given by:

$$V = Pf_2$$ Equation 7

Where P is the pixel size on sample. As described above, the speed V of the moving sample, the sample modulation, and the frame triggers can be synchronized to ensure a desired frame capture. FIG. 2C illustrates an exemplary sample modulation 203 relative to a plurality of frame triggers 204. In other embodiments, the speed of the moving sample can be generalized to be greater than or less than 1 pixel per frame interval (time duration between two consecutive frames); equation 7 is then written as:

$$V = kPf_2.$$ Equation 8

In one embodiment, k can be an integer of greater than 1, for example, k=2, 3, 4, . . . . In this case, the pixels of each frame can be binned in the scan (y) direction by the number of pixels equal to k. The effective number of pixels in the y direction is reduced by a factor of k, and equations 5 and 6 still apply as long as the image is down-sampled to the effective number of pixels. In another embodiment, k can be less than 1. For example, the sample may move half a pixel per frame interval when k=½, or one third of a pixel when k=⅓. In this case, the effective number of pixels per frame in the scan direction is increased by a factor of 1/k. The effective image may be reconstructed to larger size by re-sampling of the image through interpolation methods such as nearest neighborhood, linear, spline, or cubic interpolations. Equations 5 and 6 still apply as long as the image size in the scan direction is re-sampled to the effective number of pixels increased by the factor of 1/k. Note that the phase and amplitude can then be computed using equations 3 and 4.

Note that the sensor of the IR camera can have a rectangular format, with rectangular sensor elements (wherein a square is considered as a special case of a rectangle). In one embodiment, the sample moves at a constant speed in a direction parallel to one of the edges of the rectangular sensor. Note that P, i.e. the imaging pixel size on the sample, can be computed by the size of the sensor element along the scan direction divided by the magnification of the imaging lens.

In one embodiment of image processor 110, a technique called time delayed integration (TDI) can synchronize pixel shifting with movement of the sample. TDI is described in detail in Reissue U.S. Pat. RE 37,740, entitled "Method and apparatus for optical inspection of substrates", which issued on Jun. 11, 2002. However, in this reference, TDI captures only one instance of each imaging pixel (i.e. a line scan imaging mode). Notably, TDI can be modified to keep track of multiple captured images for each imaging pixel as the FOV moves across the sample, thereby allowing TDI to be used in the context of time delay LIT. This tracking can be performed by a computer-implemented software program installed in image processor 110.

Moreover, also in image processor 110, a single frequency Fourier filter (or matched filter, at the same frequency of modulation) in the time domain can be applied to the captured image, over a window of the multiple frames. As described above, each frame can be shifted by a predetermined number of pixels (1, 2, 3 . . . ) in the scan direction when applying the Fourier filter.

In Equations 5 and 6, each x-column i in the final image is a weighted sum from multiple frames of images, where image n contributes to this sum the column i+n−1.

By using a continuous scan of a sample, time delay LIT can advantageously eliminate the undesirable stop-go action of conventional LIT inspection systems, thereby significantly reducing inspection overhead time. Therefore, high throughput inspection in a production environment can be implemented. Notably, by varying the number of pixels moved, time delay LIT can advantageously optimize a desired speed/sensitivity balance.

Figure 3:
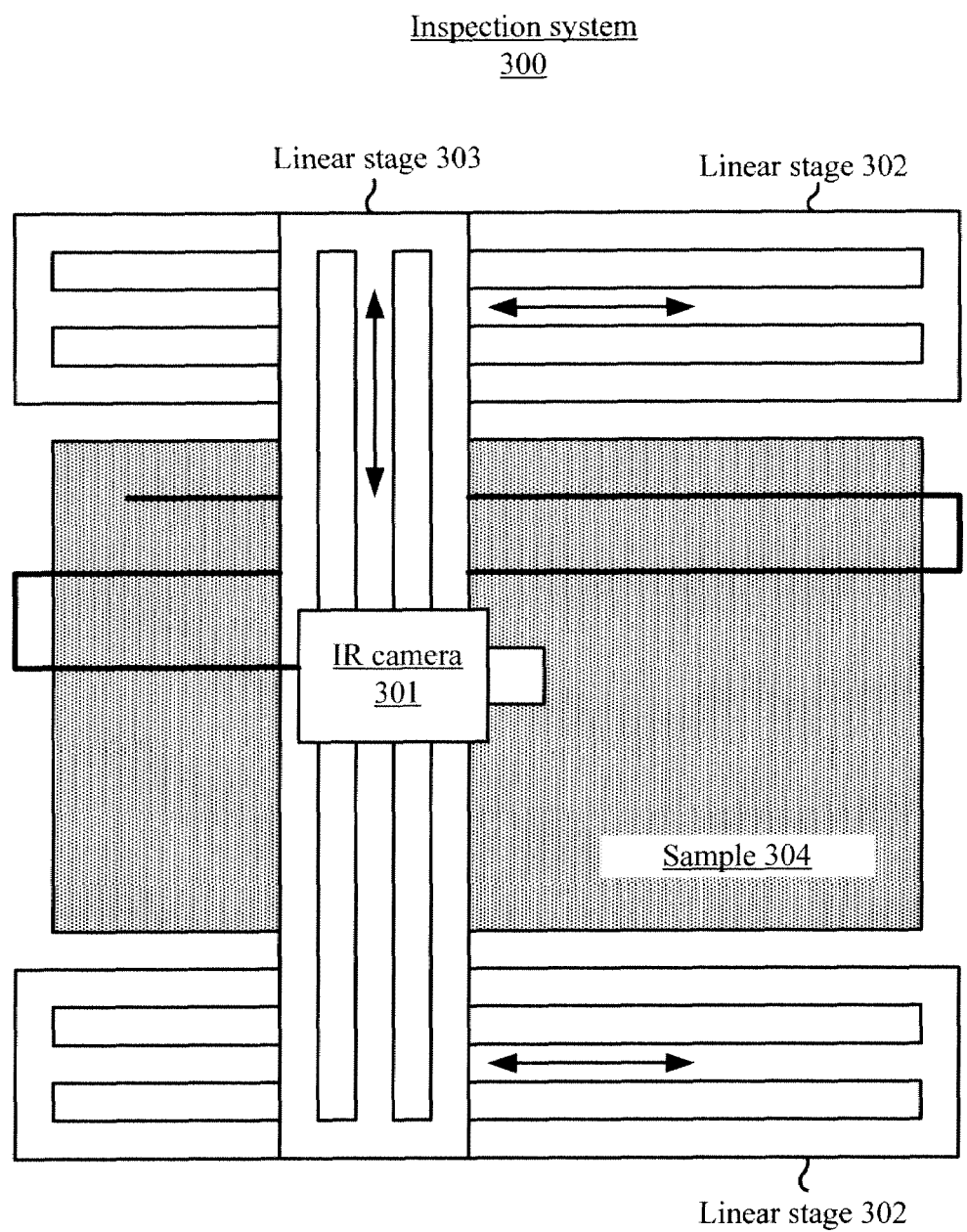
FIG. 3 illustrates an exemplary inspection system including a single IR camera that can move in both x and y directions using a gantry system.

Note that when the images of the sample are captured, the sample could be moving with respect to the IR camera (e.g. using scanning stage 102 of FIG. 1) or the IR camera could be moving with respect to the sample. For example, FIG. 3 illustrates an exemplary inspection system 300 including a single IR camera 301 that can move in both x and y directions by a gantry system, which includes linear stages 302 that allow camera movement in an x direction and a linear stage 303 that allows camera movement in a y direction. As shown in FIG. 3, alternating horizontal and vertical movements result in a serpentine scan of a sample 304.

In this embodiment, sample 304 is a single sample (e.g. a thin film, large-scale solar panel formed on a glass substrate). Note that in other embodiments using this gantry system, sample 304 could be replaced with multiple samples.

Figure 4:
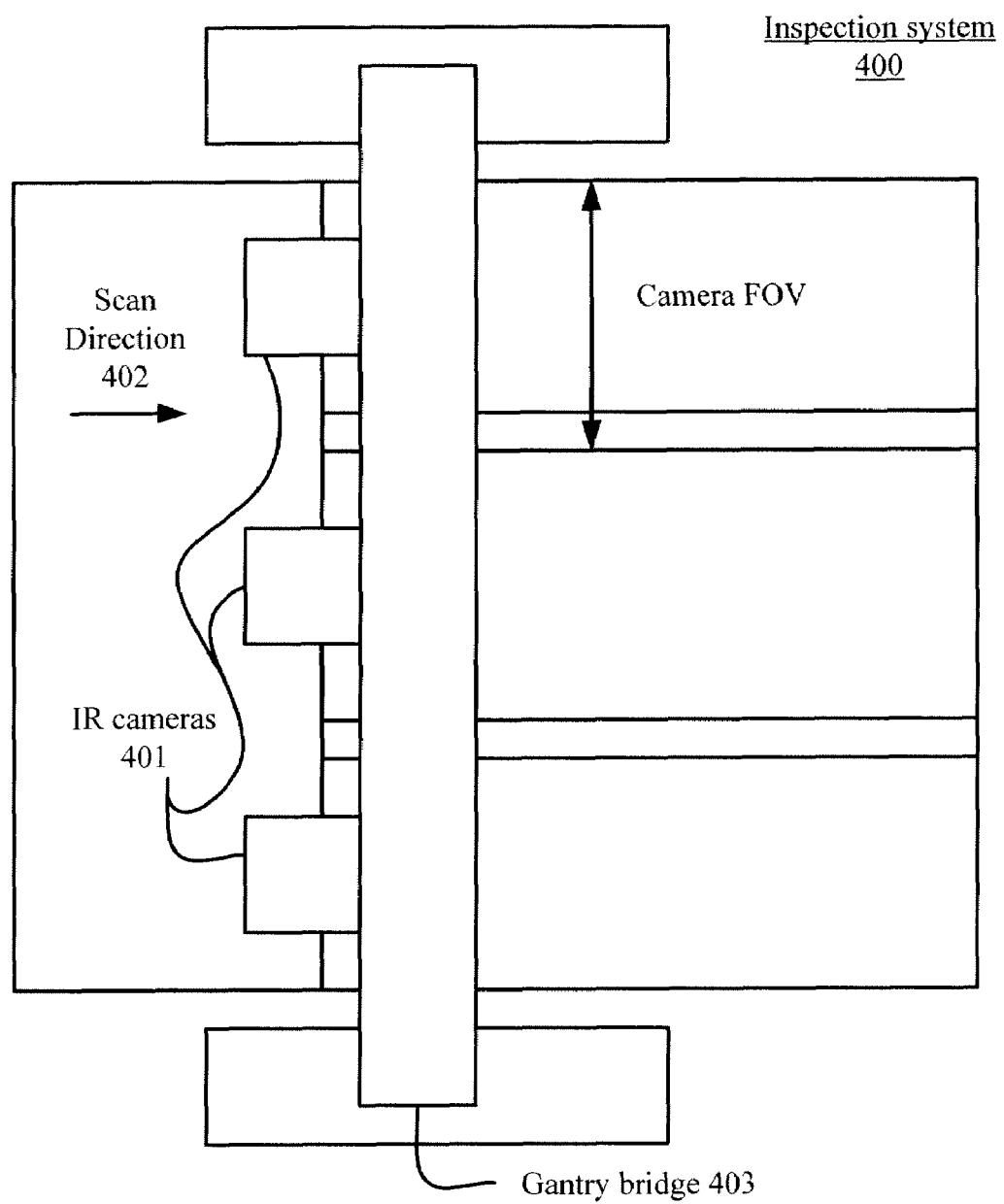
FIG. 4 illustrates an exemplary inspection system including multiple IR cameras that can move in one direction using a gantry system.

Multiple parallel IR cameras can further improve inspection speed. For example, FIG. 4 illustrates an exemplary inspection system 400 including 3 IR cameras 401, although other embodiments can include fewer or more IR cameras (note that other system components, such as those components shown in FIG. 1, are not shown for simplicity). In this embodiment, IR cameras 401 can provide a single pass scan in a direction 402 using a gantry bridge 403.

Figure 5:
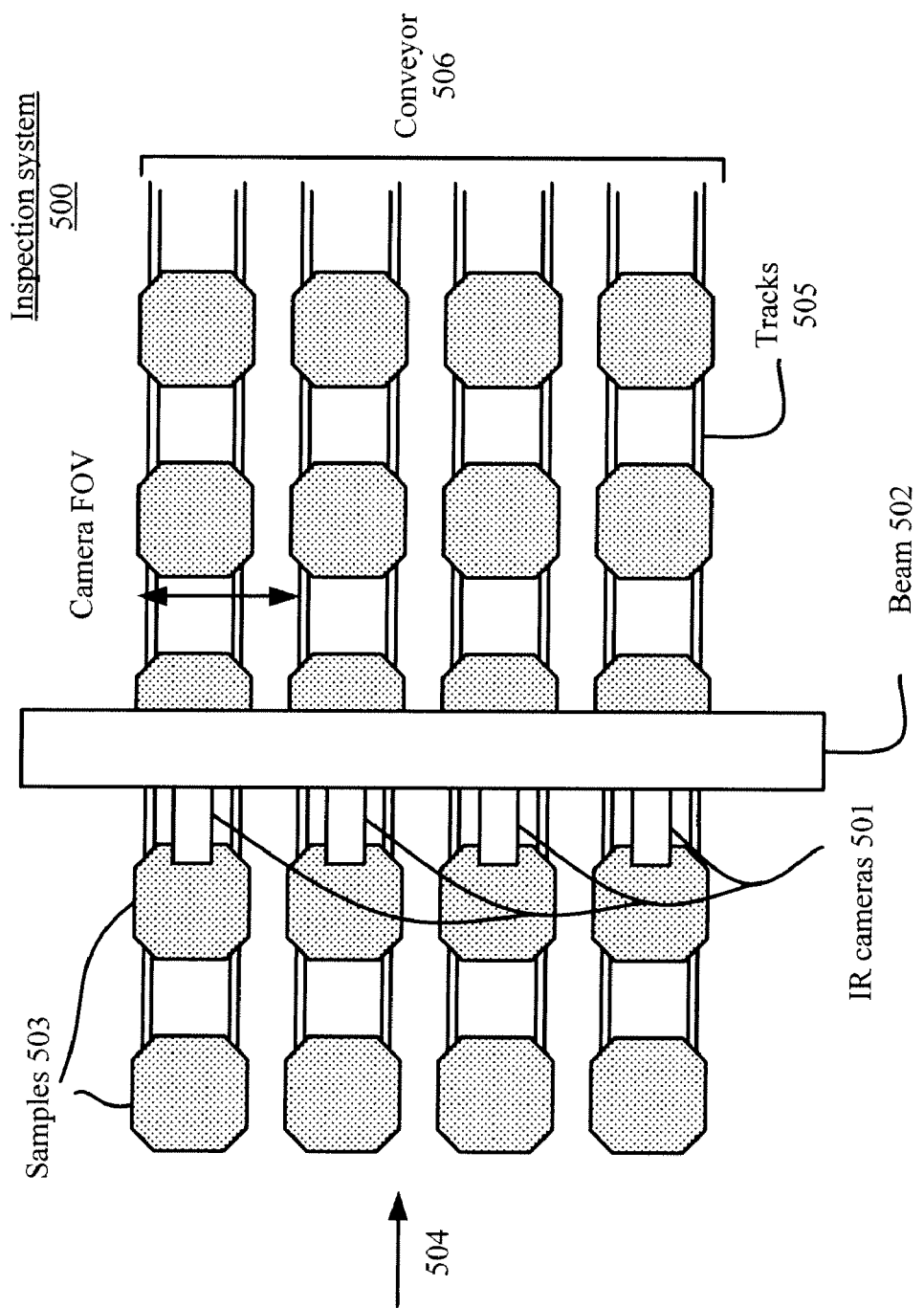
FIG. 5 illustrates an exemplary inspection system including multiple IR cameras that capture images of samples moving on a conveyor.

FIG. 5 illustrates an exemplary inspection system 500 including 4 IR cameras 501, although other embodiments can include fewer or more IR cameras. In this embodiment, IR cameras 501 can be positioned on a stationary beam 502, whereas samples 503 can move in a direction 504 using tracks 505, which form part of a conveyor 506.

In one embodiment, an IR camera can be implemented using a medium wave infrared (MWIR) camera having a sensor resolution of 320×256 pixels. The inspection system including this IR camera can include the following operating characteristics: a frame rate of 433 frames per second (fps), an imaging resolution of 0.5 mm, a sample speed of 216 mm/s, and an inspection speed of 276 cm$^2$/s.

Referring back to the time delay LIT system 100, the use of light source 103 to provide current modulation can result in some heat generation. Specifically in the case of solar cells, some portion of the illumination light is converted to heat due to the limited efficiency of solar cells to convert light power to electric power. The heat generated by the illumination can increase the background IR emission, which results in greater background noise and thus lower detection sensitivity. Notably, because the excessive heat due to illumination is generated at the same frequency as the defect signal modulation, the emissivity difference between different materials (such as metal grid lines vs. silicon) shows in the LIT image as a non-uniform background noise that may not be easily removed, thereby further reducing the defect sensitivity.

Figure 6:
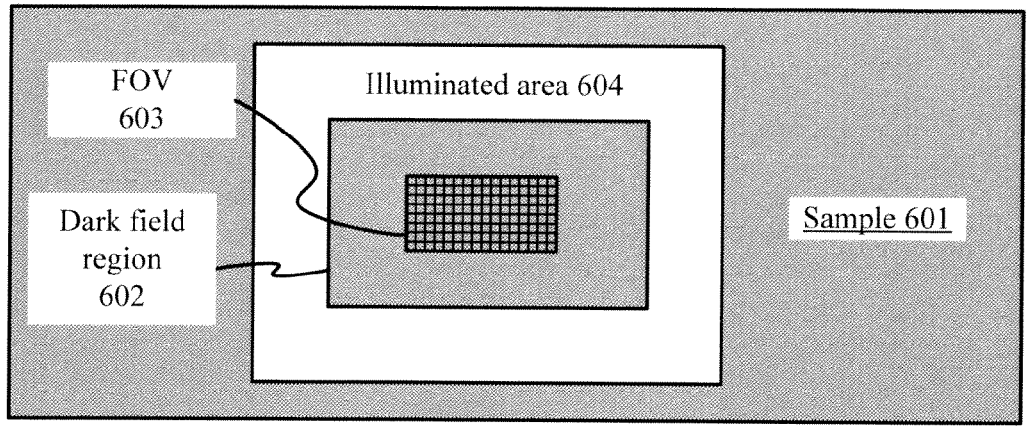
FIG. 6 illustrates an exemplary dark field illumination for the field of view (FOV) that can further minimize background noise.

Therefore, in one embodiment, system 100 can use a light shield 111 to create a dark field region for the FOV of the IR camera. In one embodiment, light shield 111 can be positioned above sample 101 by 2-4 mm, or any other distance that limits illumination of the sample. For example, FIG. 6 illustrates a dark field region 602 that could be provided by light shield 111 for protecting an FOV 603 on a sample 601. In this case, an illuminated area 604 occurs outside dark field region 602. Notably, although illuminated area 604 is limited to be outside of FOV 603, the photocurrent generated by such illumination can quickly flow into the area of FOV 603.

Therefore, the sample heating due to excessive photon energy is constrained to be outside of FOV 603. As a result, this indirect illumination advantageously minimizes the background noise inside FOV 603. However, of interest, despite using dark field region 602 for FOV 603, defects are still visible to the IR camera.

Figure 7:
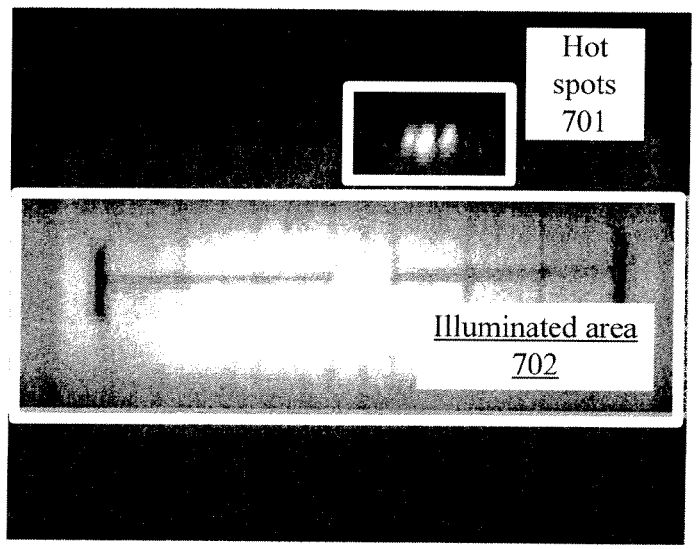
FIG. 7 illustrates an exemplary dark field FOV experimental result, wherein an expanded laser beam modulates current for an illuminated area of the sample.

For example, FIG. 7 illustrates an exemplary experimental result, wherein an expanded laser beam modulates current for an illuminated area 702 of the sample. Defects that leak current appear as hot spots 701. As shown in FIG. 7, (1) the background heating is higher where the light directly illuminates the sample, i.e. inside illuminated area 702, (2) the background heating is much lower outside illuminated area 702, and (3) the defects still appear as hot spots 701 even though they are outside illumination area 702 because current flows freely across the sample.

Referring back to FIG. 1, a predetermined area outside the FOV of IR camera 108 (e.g. a band of illumination substantially parallel to the border of the FOV) can be illuminated by light source 103 (e.g. an array of LEDs) as defined by light shield 111. Notably, light shield 111 can advantageously reduce the background heating of the FOV, thereby increasing the signal to noise ratio (SNR) of the defect in the captured images. Better SNR results in higher throughput (i.e. shorter integration times at a given sensitivity) and/or higher sensitivity.

Figure 8:
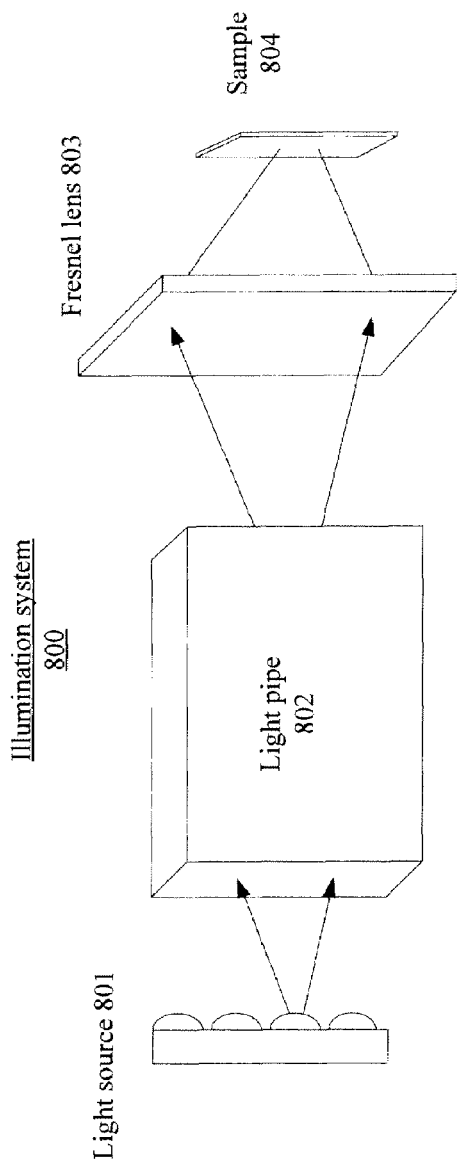
FIG. 8 illustrates an illumination system that can include a light pipe, which ensures that the light generated by a light source is efficiently relayed to a surface of the sample.

In one embodiment shown in FIG. 8, an illumination system 800 can include a light pipe 802 that can ensure that the light generated by a light source 801 is efficiently relayed to a surface of sample 804 without a light shield. Note that light pipes can be particularly effective for analyzing smaller samples, e.g. small-scale solar cells (for example, 6"×6") and semiconductor wafers, to limit light dispersion to only the samples for which images are being collected. In one embodiment, to further limit light dispersion, an optional Fresnel lens 803 can be used to focus the light from light pipe 802 onto sample 804.

Light pipe 802 can be implemented using a solid block of glass that guides the light by total internal reflection of the sidewalls of light pipe 802. In another embodiment, light pipe 802 can be implemented using a hollow tube with mirror surfaces inside. In any implementation of light pipe 802, a clearly defined illumination area (e.g. rectangular) is projected into sample 804.

Advantageously, a light pipe can be configured to cover large or small areas of a sample. In any configuration, a light pipe can provide a relatively sharply defined border for the dark field region as well as the illuminated area. For example, a light pipe could sharply define the borders of illuminated area 604 of FIG. 6 (and thus also the border of dark field region 602). In contrast, the outside border of illuminated area 604, if created by a light shield, would typically be diffused, whereas the inside border would be relatively sharply defined (assuming that the light shield is close enough to the sample).

Figure 9B:
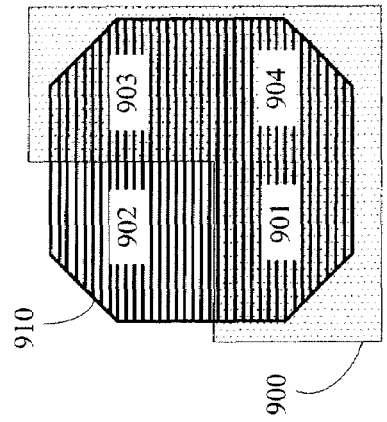
FIGS. 9A and 9B illustrate the rotation of a sample to reposition the dark field region for the FOV beneath an exemplary light pipe configuration that can be particularly efficient for smaller samples in an ILIT system.
Figure 9A:
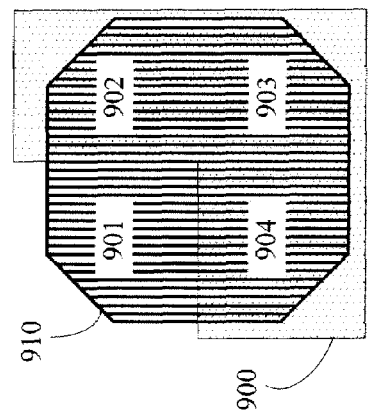

FIGS. 9A and 9B illustrate an exemplary configuration for a light pipe configuration that can be particularly efficient for smaller samples, e.g. semiconductor wafers or solar cells, in what would otherwise be a conventional LIT system. In this configuration, a sample 910 can be divided into (i.e. characterized as having) 4 quadrants, e.g. 901, 902, 903, and 904, and the shape of a light pipe 900 is substantially matched to three quadrants of sample 910. In FIG. 9A, quadrants 902, 903, and 904 are illuminated by light pipe 900, whereas quadrant 901, which is in a dark field region, can be imaged by an IR camera (not shown for simplicity). Another quadrant can be imaged by rotating sample 910 relative to light pipe 900. For example, from FIG. 9A to FIG. 9B, sample 910 is rotated counter clockwise by 90 degrees relative to light pipe 900. Thus, quadrants 901, 903, and 904 are illuminated by light pipe 900, whereas quadrant 902, which is in dark field region, can be imaged by the IR camera. Therefore, all quadrants 901, 902, 903, and 904 can be inspected by rotating sample 910 three times.

Figure 10:
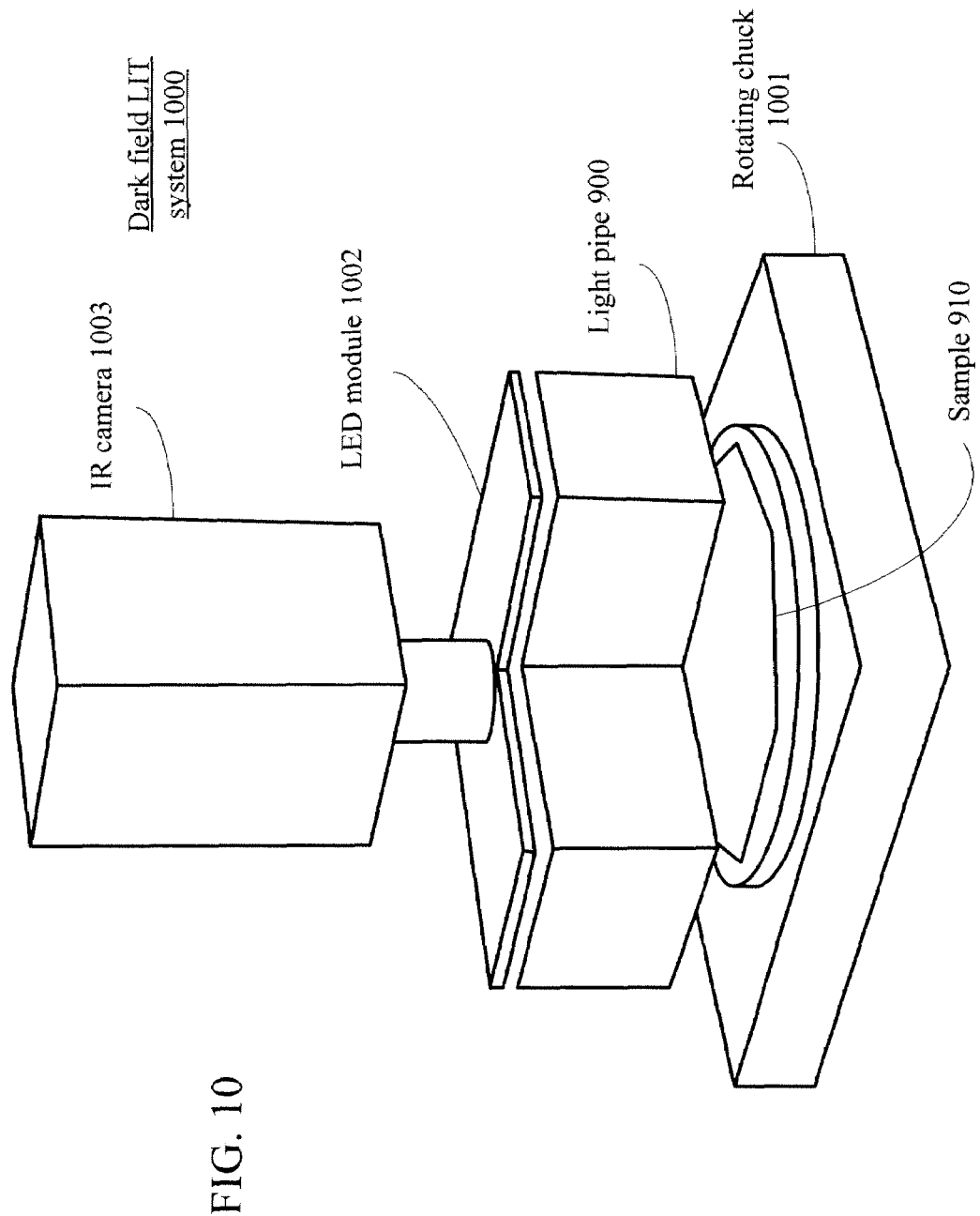
FIG. 10 illustrates an exemplary dark field ILIT system that uses the light pipe configuration of FIGS. 9A and 9B.

FIG. 10 illustrates an exemplary dark field LIT system 1000 including light pipe 900 and sample 910. In system 1000, sample 910 is positioned on a rotating chuck 1001 that can perform the desired rotations (e.g. 90 degree rotations). Light pipe 900 can direct the light from LED module 1002 onto sample 910. An IR camera 1003 can capture images from the dark field quadrant of sample 910. In this embodiment, IR camera 1003 can capture multiple shots of the dark field quadrant over time as sample 910 is current modulated by the light directed by light pipe 900. After a desired number of images have been captured by IR camera 1003, rotating chuck 1001 can be rotated to expose another quadrant of sample 910.

In other embodiments, a multi-sample dark field LIT system can be implemented. For example, FIG. 11 illustrates an exemplary configuration including four samples 1101. Block 1102 delineates the border of a dark field region. In this case, after an IR camera (not shown for simplicity) simultaneously captures the desired number of dark field images from samples 1101, then each of samples 1101 can be rotated (e.g. clockwise by 90 degrees as shown by the arrows using four chucks, not shown for simplicity) to begin capturing images from different quadrants of samples 1101.

Note that other embodiments can include different divisions of the sample. For example, FIG. 12 illustrates an exemplary configuration including a dark field region 1200 and three samples 1201, 1202, and 1203 on a conveyor belt 1204. In this case, the camera first images the left side of sample 1201 and the right side of sample 1202 within dark field region 1200. The conveyor belt 1204 next moves one sample width to the right (i.e. in a linear motion, as indicated by the arrow), and the camera images the left side of sample 1202 and the right side of sample 1203 within dark field region 1200. In another embodiment, the conveyor belt moves continuously and time delayed lock-in thermography is used to process the image as described earlier. In this embodiment, the width of the FOV must be less than the width of the sample so that part of the sample is always illuminated as the sample passes beneath the dark field region. For example, for a rectangular FPA with 320×256 pixels, the IR camera would be oriented so that the width of the cell normal to the direction of motion is covered by 320 pixels, and the width of the cell parallel to the direction of motion is covered by 256 pixels.

In one embodiment, both rotational and linear movements can be included in a dark field LIT system. For example, FIG. 13 illustrates a dark field LIT system configuration 1300 including a plurality of samples 1301 that can be positioned on rotating chucks 1304 (one shown for simplicity), which in turn can be secured to a conveyor 1303. In the configuration shown in FIG. 13, four samples 1301 can be simultaneously imaged as described in reference to FIG. 11. After the desired images are captured from all quadrants (using rotating chucks 1304), then the next four samples 1301 can be moved into position (using conveyor 1303) relative to dark field region 1302 for the next round of image capture.

Notably, as shown above, providing the dark field region for the FOV can be included in both time delay LIT and conventional LIT systems to advantageously reduce background noise when optical modulation is used. Moreover, this dark field LIT can be used for numerous types of samples, e.g. semiconductor wafers, solar cells, solar panels, PCBs, and continuous webs.

Figure 14:
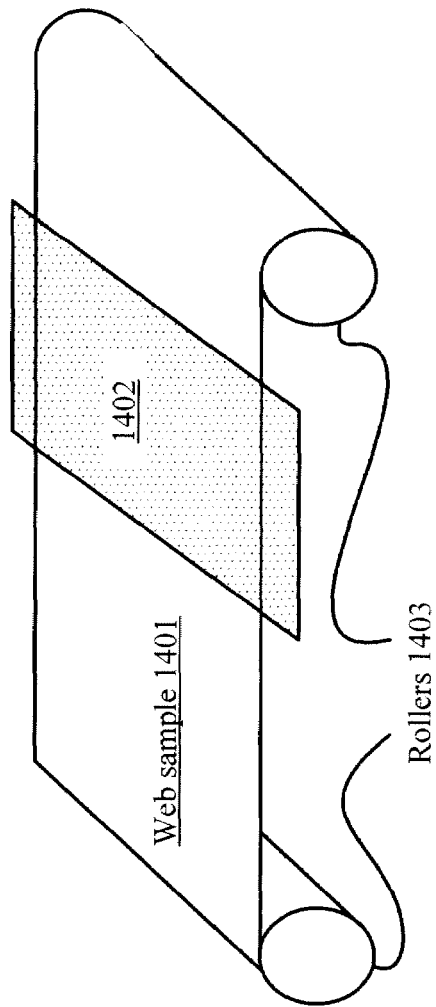
FIG. 14 illustrates a dark field ILIT in a system including at least one roller for moving a web sample.

For example, FIG. 14 illustrates an exemplary dark field LIT system 1400 in which a web sample 1401 can be advanced using rollers 1403. An exemplary web sample is a stainless steel ribbon (e.g. approximately 14 inches wide) on which photovoltaic material can be deposited. After the desired images are captured in a dark field region 1402, another portion of web sample 1401 can be positioned under dark field region 1402 using rollers 1403 and then imaged. In one embodiment, dark field LIT system 1400 could include other rollers for positioning web sample 1401 for subsequent processing (e.g. physical cutting of web sample 1401). In another embodiment, dark field LIT system 1400 can be easily converted into a time delay, dark field LIT system. That is, rollers 1403 can be used to provide the constant velocity used in a time delay LIT system. Note that other embodiments can include fewer or more rollers to provide the advancement of the web sample. Typically, a system implementation using a web sample includes at least one roller.

Although illustrative embodiments of the invention have been described in detail herein with reference to the accompanying figures, it is to be understood that the invention is not limited to those precise embodiments. They are not intended to be exhaustive or to limit the invention to the precise forms disclosed. As such, many modifications and variations will be apparent to practitioners skilled in this art.

For example, as described above for time delay LIT, when the images of the sample are captured, the sample could be moving with respect to the IR camera or the IR camera could be moving with respect to the sample. As used herein, moving an FOV of the IR camera over the sample is meant to describe either movement. Notably, either movement can provide the same captured images.

Further, note that when time delay LIT is combined with a dark field region for the inspection of multiple samples (e.g. see samples 503 of FIG. 5), then the modulation of any one sample will vary over time (because the percentage of the sample exposed to the light field (versus dark field) varies over time). However, this modulation variation can be compensated for by the appropriate programming of the image processor (e.g. see image processor 110 of FIG. 1).

Figure 15:
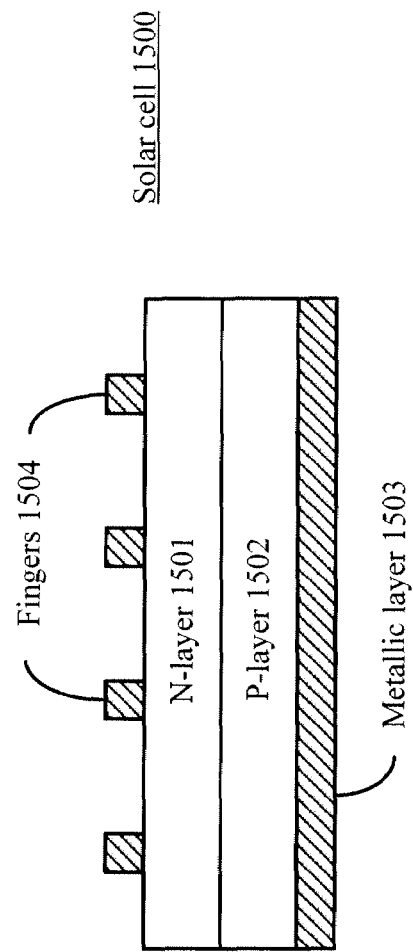
FIG. 15 illustrates aspects of a solar cell that facilitate forward biasing or reverse biasing of the solar cell during inspection.

Yet further, referring back to FIG. 15, two different electrical modulations can be performed on samples: forward bias electrical modulation and reverse bias electrical modulation. For example, in the case solar cell 1500, a reverse bias could be applied by connecting the positive terminal to N-layer 1501 (e.g. using metallic fingers 1504 on the top surface of solar cell 1500) and the negative terminal to P-layer 1502 (e.g. using a metallic layer 1503 on the back surface of solar cell 1500). In contrast, a forward bias could be applied by connecting the negative terminal to N-layer 1501 and the positive terminal to P-layer 1502. Each electrical modulation could be used to detect a different type of defect. For example, in one embodiment, the forward bias current modulation can be used to detect defects that behave more like a diode but have a low open circuit voltage.

Note that although the directed illumination configurations described herein provide a border of illumination around the FOV, other embodiments could provide different illumination shapes. That is, because current flows freely through the sample, another illumination configuration could include a plurality ($\geq 2$) of illuminated blocks distributed around the FOV that still allow modulation of the FOV.

Accordingly, it is intended that the scope of the invention be defined by the following claims and their equivalents.

The invention claimed is:

1. A method of performing time delay lock-in thermography (LIT) on a sample, the method comprising:
    moving a field of view (FOV) of an IR camera over the sample, the moving being at a constant velocity;
    providing a modulation to the sample throughout the moving;

capturing IR images using the IR camera throughout the moving, wherein moving the FOV, providing the modulation, and capturing the IR images are synchronized; and filtering the IR images to generate a time delay LIT image, thereby providing defect identification, wherein filtering includes performing two equations:

$$S_{m,i} = \frac{1}{N_Y} \sum_{n=1}^{N_Y} I_{m,n}^{(i+n-1)} \sin\left[2\pi(i-1+n-1)\frac{f_1}{f_2}\right]$$

$$C_{m,i} = \frac{1}{N_Y} \sum_{n=1}^{N_Y} I_{m,n}^{(i+n-1)} \cos\left[2\pi(i-1+n-1)\frac{f_1}{f_2}\right]$$

where i=1, 2 ..., m=1, 2, ... $N_x$, n=1, 2 ... $N_y$, $f_1$ is the frequency of modulation, $f_2$ is the frame rate, $N_x$ and $N_y$ are numbers of pixels in one frame in x and y directions.

2. The method of claim 1, wherein the modulation is one of optical and electrical.

3. The method of claim 1, wherein the sample is one of a semiconductor wafer, a solar cell, a solar panel, a continuous web, and a printed circuit board.

4. The method of claim 1, further including providing a dark field illumination for the FOV throughout the moving.

5. The method of claim 1, wherein moving includes using at least one of a scanning stage, bi-directional linear stages in a gantry system, a gantry bridge, a conveyor, and at least one roller.

6. A method of performing dark field lock-in thermography (LIT) on a sample, the method comprising:
positioning a field of view (FOV) of an IR camera within a dark field region on the sample;
providing a modulation to the sample;
capturing IR images using the IR camera,
wherein providing the modulation and capturing the IR images are synchronized; and
filtering the IR images to generate an LIT image, thereby providing defect identification, wherein filtering includes performing two equations:

$$S_{m,n} = \frac{1}{N_F} \sum_{i=1}^{N_F} I_{m,n}^i \sin\left(2\pi\frac{f_1}{f_2}(i-1)\right)$$

$$C_{m,n} = \frac{1}{N_F} \sum_{i=1}^{N_F} I_{m,n}^i \cos\left(2\pi\frac{f_1}{f_2}(i-1)\right)$$

where i=1, 2 ... $N_F$, m=1, 2, ... $N_x$, n=1, 2 ... $N_y$, $f_1$ is a frequency of modulation, $f_2$ is a frame rate (preferably an even integer multiple of $f_1$), $N_x$ and $N_y$ are the number of pixels in one frame in x and y directions, and $N_F$ is a total number of frames.

7. The method of claim 6, further including rotating the sample to reposition the FOV and the dark field region on another section of the sample, and then repeating providing the modulation, capturing the IR images, and filtering the IR images.

8. The method of claim 6, wherein the modulation is one of optical and electrical.

9. The method of claim 6, wherein the sample is one of a semiconductor wafer, a solar cell, a solar panel, a continuous web, and a printed circuit board.

10. The method of claim 6, wherein positioning and rotating include using at least one of a scanning stage, bi-directional linear stages in a gantry system, a gantry bridge, a conveyor, a rotating chuck, and at least one roller.

11. A system for performing time delay lock-in thermography (LIT) on a sample, the system comprising:
an IR camera for capturing images of the sample;
scanning components for moving a field of view (FOV) of the IR camera over the sample at a constant velocity;
modulation components for providing a modulation to the sample when moving the FOV;
a clock source for synchronizing the capturing of images, the moving of the FOV, and the providing of the modulation; and
an image processor for receiving the captured images and generating a time delay LIT image to provide defect detection,
wherein the image processor includes filters that implement two equations:

$$S_{m,i} = \frac{1}{N_Y} \sum_{n=1}^{N_Y} I_{m,n}^{(i+n-1)} \sin\left[2\pi(i-1+n-1)\frac{f_1}{f_2}\right]$$

$$C_{m,i} = \frac{1}{N_Y} \sum_{n=1}^{N_Y} I_{m,n}^{(i+n-1)} \cos\left[2\pi(i-1+n-1)\frac{f_1}{f_2}\right]$$

where i=1, 2 ..., m=1, 2, ... $N_x$, n=1, 2 ... $N_y$, $f_1$ is the frequency of modulation, $f_2$ is the frame rate, $N_x$ and $N_y$ are numbers of pixels in one frame in x and y directions.

12. The system of claim 11, further including one of a light shield and a light pipe for providing a dark field region for the FOV.

13. The system of claim 11, wherein the scanning components include at least one of a scanning stage, a conveyor, bi-direction linear stages in a gantry system, a gantry bridge, and at least one roller.

14. The system of claim 11, wherein the sample is one of a semiconductor wafer, a solar cell, a solar panel, a continuous web, and a printed circuit board.

15. A system for performing dark field, lock-in thermography (LIT) on a sample, the system comprising:
an IR camera for capturing images of the sample;
positioning components for positioning a field of view (FOV) of the IR camera over the sample;
optical modulation components for providing an optical modulation to the sample after positioning the FOV;
a light directing component for providing a dark field region for the FOV;
a clock source for synchronizing the capturing of images and the providing of the modulation; and
an image processor for receiving the captured images and generating a time delay LIT image to detect a defect on the sample, wherein the image processor includes filters that implement two equations:

$$S_{m,n} = \frac{1}{N_F} \sum_{i=1}^{N_F} I_{m,n}^i \sin\left(2\pi \frac{f_1}{f_2}(i-1)\right)$$

$$-C_{m,n} = \frac{1}{N_F} \sum_{i=1}^{N_F} I_{m,n}^i \cos\left(2\pi \frac{f_1}{f_2}(i-1)\right)$$

where $i=1, 2 \ldots N_F$, $m=1, 2, \ldots N_x$, $n=1, 2 \ldots N_y$, $f_1$ is a frequency of modulation, $f_2$ is a frame rate (preferably an even integer multiple of $f_1$), $N_x$ and $N_y$ are the number of pixels in one frame in x and y directions, and $N_F$ is a total number of frames.

16. The system of claim 15, wherein the light directing component includes a light shield.

17. The system of claim 15, wherein the light directing component includes a light pipe.

18. The system of claim 15, wherein the positioning components include at least one of a scanning stage, a conveyor, bi-direction linear stages in a gantry system, a gantry bridge, a rotating chuck, and at least one roller.

19. The system of claim 15, wherein the sample is one of a semiconductor wafer, a solar cell, a solar panel, a continuous web, and a printed circuit board.

* * * * *